US00PP18618P2

(12) United States Plant Patent
Alston

(10) Patent No.: US PP18,618 P2
(45) Date of Patent: Mar. 18, 2008

(54) APPLE ROOTSTOCK TREE NAMED 'M116'

(50) Latin Name: *Malus pumila Mill*
Varietal Denomination: M116

(75) Inventor: Frank Alston, Maidstone (GB)

(73) Assignee: Horticulture Research International, Kent (GB)

( * ) Notice: Subject to any disclaimer, the term of this patent is extended or adjusted under 35 U.S.C. 154(b) by 742 days.

(21) Appl. No.: 10/303,484

(22) Filed: Nov. 25, 2002

(30) Foreign Application Priority Data

Nov. 26, 2001 (NZ) ..... APR 21

(51) Int. Cl.
*A01H 5/00* (2006.01)

(52) U.S. Cl. ..... Plt./174

(58) Field of Classification Search ..... Plt./174, Plt./161
See application file for complete search history.

(56) References Cited

PUBLICATIONS

Webster et al., Compact Fruit Tree (2000), vol. 33, No. 4, pp. 100–104.*
Webster et al, Acta Horticulturae (1997), No. 451, pp. 83–88.*

* cited by examiner

*Primary Examiner*—Wendy C. Haas
*Assistant Examiner*—Georgia Helmer

(57) ABSTRACT

A new and distinct variety of Apple Rootstock Tree named 'M116' (nonpatented) characterized by improved resistance to collar rot, mildew and specific replant disease.

3 Drawing Sheets

Botanical classification: *Malus pumila* Mill.
Variety denomination: 'M116' (nonpatented).

BACKGROUND OF THE INVENTION

In 1962 and 1964, two rootstocks of apple (*Malus pumila* Mill.), 'Malling-Merton 106' (nonpatented) (Seed parent) and 'Malling 27' (nonpatented) (pollen parent), both not patented, were crossed in a cultivated area of West Malling, Kent, England. These crosses produced 56 (AR10 series) and 59 (AR86 series) seedlings, respectively. After the completion of preliminary screening tests, eight seedlings from the AR10 series and seven from the AR86 series were selected and propagated in 1973 for further evaluation. The vigour of each selection, when grown as hard-pruned hedges in the nursery, was recorded between 1979 and 1983. The potential vigour of the selections when used as rootstocks was estimated from measurements of the percentage of bark tissue in young roots, using techniques first described by Beakbane and Thompson (1947) and later modified by Werts et al. (1976). This percentage root bark was measured a number of times between 1974 and 1980 on root samples from all of the 15 selections. One of the seedlings, 'AR 86-1-25' (nonpatented) had 52% rootbark.

The ability of these selections to root and establish from hardwood cuttings was assessed in a minimum of six separate propagation trials conducted during 10 years. In each test the rooting and subsequent establishment of hardwood cuttings of each selection were evaluated using techniques developed at East Malling Research Station (Howard, 1971). For 'AR86-1-25' (nonpatented), 63% of cuttings rooted and established in the field.

The incidence of mildew (*Podosphaera leucotricha*) was observed over several years on most of the selections growing as hedges and receiving the standard East Malling Research Station nursery spray programme for pests and diseases. 'AR86-1-25' (nonpatented) was found to be relatively resistant. The selections were scored for resistance to woolly apple aphid (*Eriosoma lanigerum*) in tests on small potted specimens grown under glass (Lyth and Watkins, 1981). The rating of 'AR86-1-25' (nonpatented) was inconclusive but it has since been recorded as resistant. The selections were also scored for resistance to collar-rot (*Phytophthora cactorum*). 'AR86-1-25' (nonpatented) was rated as fairly resistant. Finally, the field resistance of many of the selections to specific apple replant disease (SARD) was evaluated (Oehl and Jackson, 1980). 'AR86-1-25' (nonpatented) was considered resistant.

'AR86-1-25' (nonpatented) was first asexually reproduced in 1973 in East Malling, Kent, England by hardwood cuttings and subsequent generations have been true to phenotype.

SUMMARY OF THE INVENTION

Rooted cuttings of 'AR86-1-25' (nonpatented) were lined out and budded with 'Cox's Orange Pippin' (nonpatented) in 1974. The maiden trees were planted at 3 m×5 m in a replicated design with eight randomised blocks in February 1976 at East Malling. 'Malling 9 (nonpatented, 'Malling 26' (nonpatented) and 'Malling-Merton 106' (nonpatented) were also lined out and budded with 'Cox's Orange Pippin' (nonpatented) in 1974 and planted in the orchard for comparison. A weed-free strip 2 meters wide was maintained beneath the tree rows. The trees were minimally pruned and trained as open centre bushes. Shoot growth, floral buds, fruit set and yields were recorded on various occasions and the weight of the above ground portion of each tree recorded at grubbing.

'AR86-1-25' (nonpatented) produced trees of similar or slightly smaller size than those on 'Malling-Merton 106' (nonpatented) and bore abundant flowers which set fruit efficiently. Yield and fruit grade-out for 'Cox's Orange Pippin' (nonpatented) on 'AR86-1-25' (nonpatented) were better than for 'Malling-Merton 106' (nonpatented). The 5 year cumulative total yields of 'Cox's Orange Pippin' (nonpatented) were higher on 'AR86-1-25' (nonpatented) than on MM.106 (82 kg compared to 68 kg) 'AR86-1-25' (nonpatented) exhibits improved resistance to collar rot and specific apple replant disease than 'Malling-Merton 106' (nonpatented). From the trial evidence, it was concluded that 'AR86-1-25' (nonpatented) could provide an improved rootstock over 'Malling-Merton 106' (nonpatented).

In a trial conducted in Hawkes Bay, New Zealand, the number of flower clusters per unit tree size of Royal 'Gala' (nonpatented) has been similar for trees on M.116 and MM.106 (7–8 spur and terminal clusters per unit trunk cross sectional area). However, in a trial conducted in Central Otago, New Zealand, spur abundance was slightly lower for trees on M.116 compared with trees on MM.106. Cumulative yields and yield efficiencies were similar for Royal 'Gala' (nonpatented) trees on 'M116' (nonpatented) and MM.106 in the Hawkes Bay, New Zealand trial.

'M116' (nonpatented) is different from the pollen parent Malling 27 in that 'M116' (nonpatented) has larger flowers and a green-brown bark 199A/152A. The bark of 'Malling 27' (nonpatented) is brown 200C.

On the basis of the testing carried out in the UK and New Zealand it was considered that 'AR86-1-25' (nonpatented) was a commercially useful rootstock and the Policy Group of the HRI Apple and Pear Breeding Club decided to release it under the name M116. 'M116' nonpatented) has not been observed under all possible environmental conditions and its phenotype may vary significantly with variations in environment such as temperature, light intensity, and day length, without any variation in genotype. However, the following unique combination of characteristics relating to the use of 'M116' (nonpatented) as a rootstock for apple varieties, distinguish 'M116' (nonpatented) from all other apple varieties known to the inventor.

1. Improved resistance to collar rot, mildew and specific apple replant disease;
2. Compatible as a rootstock with all apple varieties tested;
3. Improved yields over Malling-Merton 106' (nonpatented);
4. Semi-vigorous growth.

DESCRIPTION OF THE DRAWINGS

'M116' (nonpatented) is illustrated by the accompanying photographic drawings, depicting the plant by the best possible color representation using conventional color photography techniques. Although the colors in the photographs may appear different from actual colors due to light reflectance, they are as accurate as possible by conventional photography. The photos are of trees and fruit grown at West Malling, Kent, England.

BOTANICAL DESCRIPTION OF THE PLANT

Figure 1:
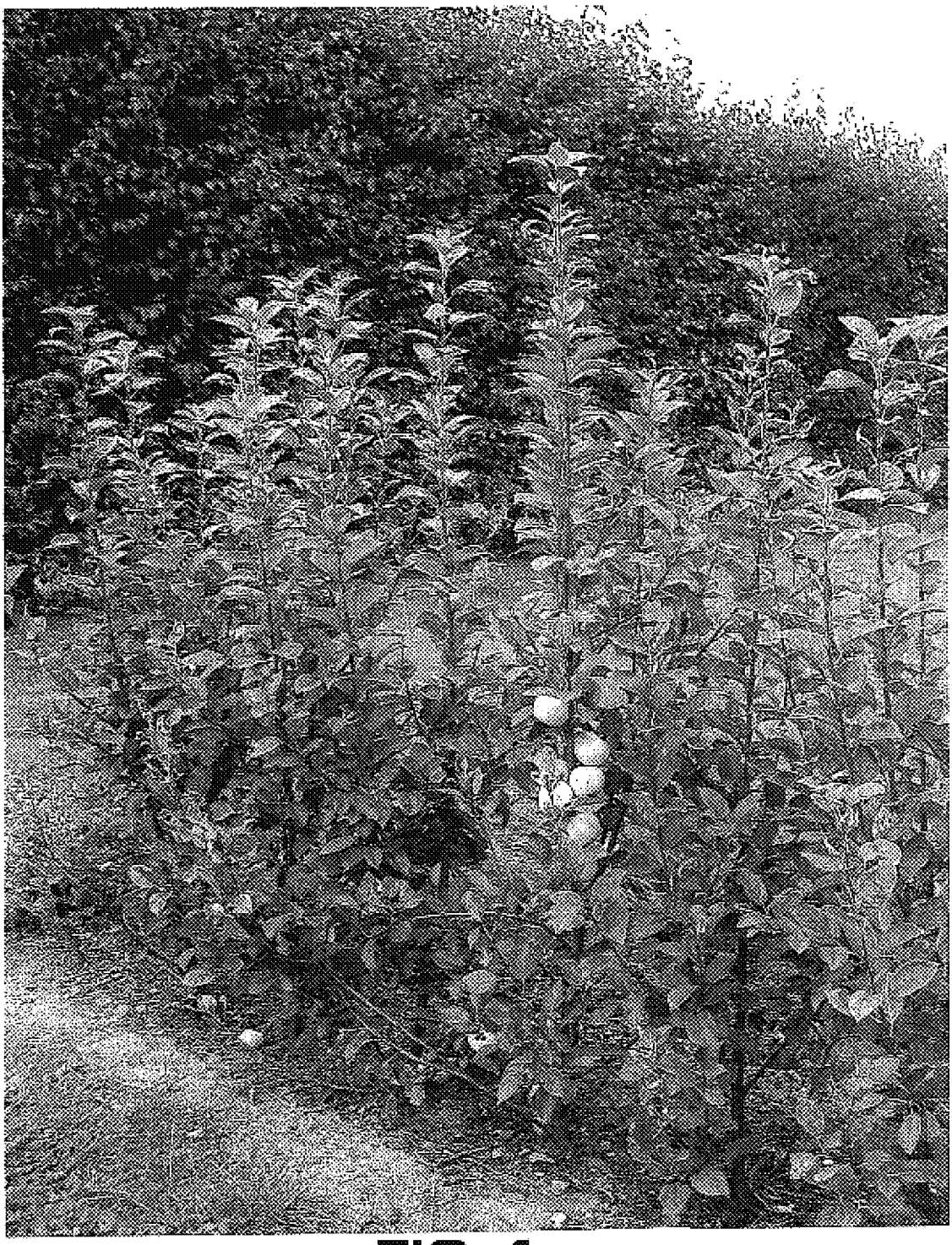
FIG. 1 shows an overall view of a 3 year old tree.
Figure 2:
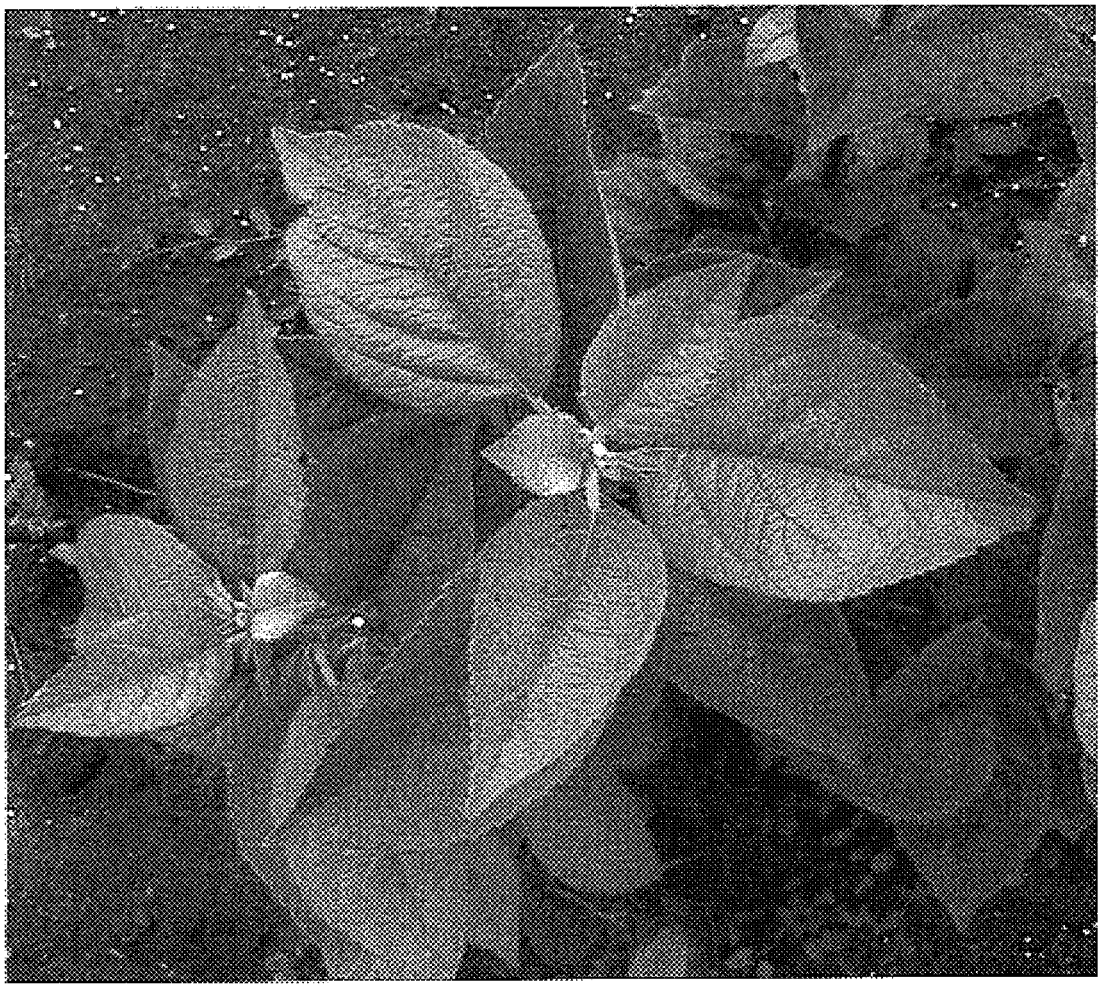
FIG. 2 is a close up view of the leaves.
Figure 3:
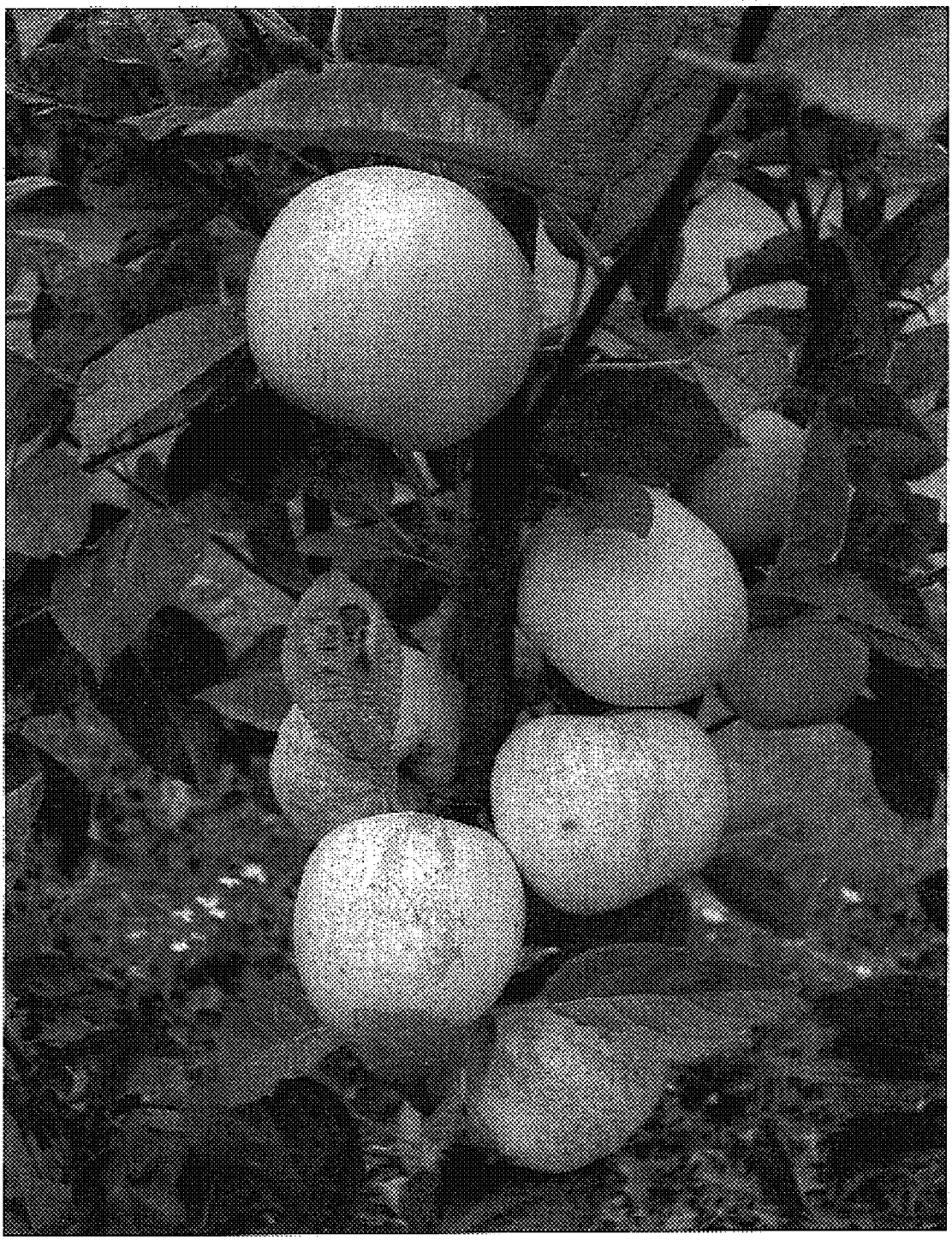
FIG. 3 is a close up side view of the fruit.

The following is a detailed botanical description of the new cultivar of *Malus pumila* Mill. named 'M116'. Observations, measurements, values, and comparisons were collected in West Malling, Kent, England from a 9 year old tree grown in full sun and on 1 year old shoots.

Terminology used is in accordance with Michael Hickey and Clive King: The Cambridge Illustrated Glossary of Botanical Terms, 2000 Cambridge University Press.

'M116' has not been observed under all possible environmental conditions. The phenotype may vary with variations in the environment such as temperature and light level, without, however, any variance in genotype. Color references are made to The Royal Horticultural Society Colour Chart except where general terms of ordinary dictionary significance are used.

Botanical classification: *Malus pumila* Mill.
Variety denomination: 'M116' (nonpatented).
Common name: Apple Rootstock.
Parentage:
- *Pollen parent.*—'Malling 27' (nonpatented).
- *Seed parent.*—'Malling Merton 106' (nonpatented).

Propagation: Hardwood Cuttings and Layering.
Type: Medium deciduous tree.
Use: Rootstock.
Vigour: Vigorous.
Hardiness: Has been found to tolerate UK climatic conditions with temperatures typically in the range −5° C. to +30° C. Zone 4–9.
Root system: Wide spreading.
Suckering: Initial trials show M.116 has a low tendency to sucker.
Dwarfing: Slightly more dwarfing that MM.106 but significantly more vigorous than M.26.
Precocity: Precocity of flowering and cropping is generally similar on M.116 and MM.106.
Tree:
- *Habit.*—Upright-spreading.

Trunk:
- *Girth.*—Medium, moderately rough.
- *Color.*—Green-brown 199A/152A.

Branches:
- *Surface texture.*—Smooth.
- *Crotch angle.*—60 degrees.
- *Color: Green-brown* 199A/152A.
- *Form.*—Profuse branching.

Lenticels:
- *Quantity.*—Medium (upper third of shoot).
- *Length.*—0.5–0.7 mm.
- *Width.*—0.5 mm.
- *Color.*—166D.

Young shoots:
- *Bark colour: Red-brown* 183A/200B.
- *Pubescence.*—Strong (upper third of shoot).
- *Internode length.*—Short — medium 20–25 mm.

Buds:
- *Position of buds in relation to shoot.*—Adpressed.
- *Size.*—3 mm in length and 2 mm in width.
- *Colour.*—Dark brown 200B.
- *Pubescence.*—Present.

Leaves:
- *Length.*—75–85 mm.
- *Width.*—45–55 mm.
- *Shape.*—Ovate.
- *Shape of base.*—Rounded.
- *Apical angle.*—Obtuse.
- *Shape of tip.*—Acuminate.
- *Arrangement.*—Alternate.
- *Colour of upper side.*—Medium green 147A.

*Colour of lower side.*—Light green 137C/D.
*Pubescence of lower side.*—Medium-strong.
*Serrations of margin.*—Bluntly serrate or biserrate.

Petiole:
*Petiole length: Average* 25 mm.
*Petiole diameter.*—2.5 mm.
*Petiole color.*—147C changing to 183C toward the base.
*Stipule size.*—10 mm in length and 2 mm in width.
*Stipule color.*—Upper 143A, lower 148B.

Flowers:
*Dates of first and full blossoms.*—April 21 and 26, near West Malling, Kent, England. Early-midseason bloom period.
*Size.*—45 mm in diameter.
*Color: White, RHS* 155A both surfaces with pink veins 66D.
*Petal shape.*—Broad ovate.
*Petal length.*—18–20 mm.
*Petal number.*—5.
*Petal width.*—13 mm.
*Petal margin.*—Entire.
*Petal texture: Smooth.*
*Petal base.*—Cuneate.
*Sepal dimensions.*—8–10 mm in length and 2 mm in width.
*Sepal position.*—Reflexed.
*Stigma position as compared with the anthers.*—73% Stigma is same level as Anthers, 27% slightly lower than Anthers.
*Stigma color.*—1C.
*Anther size.*—10.2 mm.
*Anther number.*—15.
*Anther colour.*—8C.
*Pollen amount.*—Moderate.
*Pollen colour.*—8B.
*Pollination.*—Low self-fertilization, needs pollinizer with overlapping bloom period.

Fruit:
*Size medium.*—Width 70 mm, height 60 mm.
*Shape.*—Globose conical.
*Position of maximum diameter.*—In the middle.
*Ribbing.*—Distinct rounded ribs. Eye with weak crowning.
*Size of eye.*—Small-medium.
*Aperture of eye.*—Closed.
*Eye basin.*—Medium width (20–25 mm), medium depth (5 mm); slightly ribbed with beading present in some fruit.
*Sepals.*—Medium length 7.5 mm, 3.5 mm in width, broad and overlapping.
*Sepal color.*—138 B/C.
*Stalk.*—Medium-long, average 25 mm in length.
*Stalk color.*—175A/177A.
*Thickness of stalk.*—Medium, 2.5 mm in width.
*Stalk cavity.*—Width — broad (35 mm) and depth — medium-deep (14 mm).
*Skin.*—Smooth, not greasy.
*Ground colour of skin.*—Pale green 145D changing to yellow 10D.
*Overcolour of skin.*—Small area of pale orange flush 39A with red pink lenticels 39B/50B on the sunny side, lenticels small and brown 165A but not prominent on the shaded side.
*Russet.*—Very small amount confined within the stalk cavity.
*Flesh color.*—Cream 150D.
*Fruit in cross section.*—Aperture of locules — half-open.
*Flavor.*—Sweet.
*Aroma.*—Mild.
*Eating quality.*—No commercial value.
*Seed shape.*—Broad ovate.
*Seed colour.*—Light brown 177B/200D.

Resistance to insects: Resistant to woolly apple aphid (*Eriosoma lanigerum*).

Resistance to diseases: Excellent, resistant to collar rot (*Phytophthora cactorum*), mildew (*Podosphaera leucotricha*) and the specific replant disease.

Hardiness: Winter hardy, drought and heat tolerant.

Graft compatibility: 'M116' (nonpatented) is fully compatible with 'Cox's Orange Pippin' (nonpatented) and 'Gala' (nonpatented). 'M116' (nonpatented) exhibits good union between the root-stock and the grafting stock (scion) with no rejection tendencies observed to date.

It is claimed:

1. A new and distinct variety of Apple Rootstock Tree named 'M116' (nonpatented) as described and illustrated.

* * * * *